United States Patent [19]

Brakenhoff et al.

[11] Patent Number: 5,723,120

[45] Date of Patent: Mar. 3, 1998

[54] METHOD OF TREATING AN IL-6 RELATED DISEASE WITH INTERLEUKIN-6 RECEPTOR ANTAGONISTS

[75] Inventors: Just P. J. Brakenhoff, Amsterdam; Lucien A. Aarden, Broek In Waterland, both of Netherlands

[73] Assignees: Chiron Corporation, Emeryville, Calif.; Central Laboratory of the Netherlands Red Cross Blood Transfusion Service, Amsterdam, Netherlands

[21] Appl. No.: 476,651

[22] Filed: Jun. 7, 1995

Related U.S. Application Data

[62] Division of Ser. No. 357,538, Dec. 16, 1994, Pat. No. 5,591,827, which is a continuation of Ser. No. 959,942, Oct. 20, 1992, abandoned.

[51] Int. Cl.$^6$ .......................... A61K 38/19; C07K 14/54
[52] U.S. Cl. ................ 424/85.2; 514/2; 514/12; 514/885; 530/351
[58] Field of Search .................. 424/85.2; 514/2, 514/885, 12; 530/351

[56] References Cited

U.S. PATENT DOCUMENTS

| | | | |
|---|---|---|---|
| 4,179,337 | 12/1979 | Davis et al. | 435/181 |
| 4,399,216 | 8/1983 | Axel et al. | 435/6 |
| 4,495,285 | 1/1985 | Shimuzu et al. | 435/215 |
| 4,511,502 | 4/1985 | Builder et al. | 260/112 R |
| 4,530,787 | 7/1985 | Shaked et al. | 260/112 R |
| 4,569,790 | 2/1986 | Koths et al. | 260/112 R |
| 4,572,798 | 2/1986 | Koths et al. | 260/112 R |
| 4,603,106 | 7/1986 | Cerami et al. | 435/7 |
| 4,609,546 | 9/1986 | Hiratani | 424/83 |
| 4,620,948 | 11/1986 | Builder et al. | 530/419 |
| 4,683,195 | 7/1987 | Mullis et al. | 435/6 |
| 4,683,202 | 7/1987 | Mullis | 435/91 |
| 4,711,845 | 12/1987 | Gelfand et al. | 435/68 |
| 4,748,234 | 5/1988 | Dorin et al. | 530/412 |
| 4,766,106 | 8/1988 | Katre et al. | 514/12 |
| 4,847,201 | 7/1989 | Kawasaki et al. | 435/70 |
| 4,929,700 | 5/1990 | Halenbeck et al. | 530/351 |
| 4,966,852 | 10/1990 | Wun et al. | 435/235 |
| 5,210,075 | 5/1993 | Scholz et al. | 514/14 |
| 5,470,952 | 11/1995 | Stahl et al. | 530/350 |

FOREIGN PATENT DOCUMENTS

| | | |
|---|---|---|
| 268110 A1 | 5/1988 | European Pat. Off. |
| 270799 A1 | 6/1988 | European Pat. Off. |
| 4-008296 A | 1/1992 | Japan |
| 5-097892 A | 4/1993 | Japan |
| WO 85/04899 | 11/1985 | WIPO |
| WO 91/08774 | 6/1991 | WIPO |
| WO 92/21029 | 11/1992 | WIPO |

OTHER PUBLICATIONS

Bataille et al., "Biologic Effects of Anti–Interleukin–6 Murine Monoclonal Antibody in Advanced Multiple Myeloma," *Blood*, 86: 685–691 (1995).

Emilie et al., "Administration of an Anti–Interleukin–6 Monoclonal Antibody to Patients with Acquired Immunodeficiency Syndrome and Lymphoma: Effect on Lymphoma Growth and on B Clinical Symptoms," *Blood*, 84: 2472–2479 (1994).

Gennari et al., "Anti–Interleukin–6 antibody treatment improves survival during gut–derived sepsis in a time–dependent manner by enhancing host defense," *Critical Care Medicine*, 23: 1945–1953 (1995).

Gennari et al., "Effects of Antimurine Interleukin–6 on Bacterial Translocation During Gut–Derived Sepsis," *Arch. Surg.*, 129: 1191–1197 (1994).

Lu et al., "Measurement of Whole Body Interleukin–6 (IL–6) Production: Prediction of the Efficacy of Anti–IL–6 Treatments," *Blood*, 86:3123–3131 (1995).

Starnes et al., "Retraction," *J. Immunol.*, 148: 1968 (1992).

Suzuki et al., "Anti–human Interleukin–6 receptor antibody inhibits human myeloma growth in vivo," *Eur. J. Immunol.* 22: 1989–1993 (1992).

Van Bladel et al., "Interleukin–6 Enhances the Expression of Tumor Necrosis Factor Receptors on Hepatoma Cells and Hepatocytes," *Cytokine*, 3:149–154 (1991).

Wendling et al., "Treatment of Severe Pheumatoid Arthritis by Anti–Interleukin 6 Monoclonal Antibody," *J. Rheumatol.*, 20:259–262 (1993).

Aarden et al., "Production of hybridoma growth factor by human monocytes", *Eur. J. Immunol.*, 17:1411–1416 (1987).

Arcone et al., "Internal deletions of amino acids 29–42 of human interleukin–6 (IL–6) differentially affect bioactivity and folding", *FEBS Letters*, 288(1.2):197–200 (1991).

Arcone et al., "Single–Step purification and structural characterization of human interleukin–6 produced in *Escherichia coli* from a T7 RNA polymerase expression vector", *Eur. J. Biochem.*, 198:541–547 (1991).

Bauer et al., "Interleukin–6 in Clinical Medicine", *Ann. Hematol.*, 62:203–210 (1991).

Bolivar et al., "Construction And Characterization Of New Cloning Vehicles", *Gene*, 2:95–113 (1977).

Brakenhoff et al., "Analysis of Human IL–6 Mutants Expressed in *Eschericia coli*: Biological Activities Are Not Affected by Deletion of Amino Acids 1–28", *J. Immunol.*, 143(4):1175–1182 (1989).

(List continued on next page.)

Primary Examiner—John Ulm
Assistant Examiner—Prema Mertz
Attorney, Agent, or Firm—Li-Hsien Rin-Laures; Paul B. Savereide; Robert P. Blackburn

[57] ABSTRACT

This invention provides a class of interleukin-6 (IL-6) muteins which act as IL-6 receptor antagonists, thereby inhibiting the normal function of naturally-occurring IL-6. These IL-6 receptor antagonism are preferably IL-6 molecules containing one or more mutations in the Site II region comprising amino acids 154–163. This invention also provides pharmaceutical compositions comprising IL-6 receptor antagonists with a pharmaceutically acceptable carrier. This invention further provides methods for treating IL-6 related diseases such as sepsis and multiple myeloma, the methods comprising administering to a patient an IL-6 receptor antagonist.

8 Claims, 5 Drawing Sheets

OTHER PUBLICATIONS

Brakenhoff et al., "Construction of an Interleukin–6 Antagonist", *Cytokine*, 3(5):496 (Sep. 1991)(Abstract Only).

Brakenhoff et al., "Molecular Cloning and Expression of Hybridoma Growth Factor in *Escherichia coli*", *J. Immunol.*, 139(12):4116–4121 (1987).

Brakenhoff et al., "Structure–Function Analysis of Human IL–6 Epitope: Mapping of Neutralizing mAB Recognizing Two Distinct Sites on IL–6", *Lymphokine Research*, 9(4):588 (Winter 1990) (Abstract Only).

Brakenhoff et al., "Structure–Function Analysis of Human IL–6: Epitope Mapping of Neutralizing Monoclonal Antibodies with Amino–and Carboxyl–Terminal Deletion Mutants", *J. Immunol.* 145(2):561–568 (1990).

Broach, "Construction of High Copy Yeast Vectors Using 2–μm Circle Sequences", *Meth. Enzymol.*, 101:307–325 (1983).

Broach et al., "Transformation in Yeast: Development of a Hybrid Cloning Vector and Isolation of the CAN1 Gene", *Gene*, 8:121–133 (1979).

Campbell et al., "Essential Role for Interferon–γ and Interleukin–6 in Autoimmune Insulin–Dependent Diabetes in NOD/Wehi Mice", *J. Clin. Invest.*, 87:739–742 (1991).

Clarke et al., "Selection Procedure for Isolation of Centromere DNAs From *Saccharomyces cerevisiae*", *Meth. Enzymol.*, 101:300–307 (1983).

Clewell, "Nature of Col $E_1$ Plasmid Replication in *Escherichia coli* in the Presence of Chloramphenicol", *J. Bacteriol.*, 110(2):667–676 (1972).

Clewell et al., "Supercoiled Circular DNA–Protein Complex in *Escherichia coli*: Purification and Induced Conversion to an Open Circular DNA Form", *Proc. Nat'l Acad. Sci.*, U.S.A., 62:1159–1166 (1969).

Clogston et al., "Disulfide Structures of Human Interleukin–6 Are Similar to Those of Human Granulocyte Colony Stimulating Factor", *Arch. Biochem. Biophys.*, 272(1):144–151 (1989).

Cohen et al., "Nonchromosomal Antibiotic Resistance in Bacteria: Genetic Transformation of *Escherichia coli* by R–Factor DNA", *Proc. Nat'l Acad. Sci.*, U.S.A. 69(8):2110–2114 (1972).

Coulie et al., "High–Affinity binding sites for human 26–kDa protein (interleukin 6, B cell stimulatory factor–2, human hybridoma plasmacytoma growth factor, interferon–$α_2$), different from those of type I interferon ($α,β$,) on lymphoblastoid cells", *Eur. J. Immunol.*, 17:1435–1440 (1987).

Depicker et al., "Nopaline Synthase: Transcript Mapping and DNA Sequence", *J. Mol. Appl. Gen.*, 1:561–573 (1982).

Derbyshire et al., "A simple and efficient procedure for saturation mutagenesis using mixed oligodeoxynecleotides", *Gene*, 46:145–152 (1986).

Eldering et al., "Expression of Functional Human C1 Inhibitor in COS Cells", *J. Biol. Chem.*, 263(24)11776–11779 (1988).

Fiers et al., "Complete nucleotide sequence of SV40 DNA", *Nature*, 273:113–120 (1978).

Fiorillo et al., "Analysis of human/mouse interleukin–6 hybrid proteins: both amino and carboxy termini of human interleukin–6 are required for in vitro receptor binding", *Eur. J. Immunol.*, 22:2609–2615 (1992).

Fontaine et al., "Internal deletions in human interleukin–6: structure–function analysis", *Gene*, 104:227–234 (1991).

Gearing et al., "The IL–6 Signal Transducer, gp130: An Oncostatin M Receptor and Affinity Converter for the LIF Receptor", *Science*, 255:1434–1437 (1992).

Goeddel et al., "Synthesis of human fibroblast interferon by *E. coli*", *Nucl. Acids Res.* 8(18):4057–4074 (1980).

Graham et al., "A New Technique for the Assay of Infectivity of Human Adenovirus 5 DNA", *Virology*, 52:456–467 (1973).

Grau, "Implications of cytokines in immunopathology: experimental and clinical data", *Eur. Cytokine Net.*1(4):203–210 (1990).

Grau et al., "Interleukin 6 Production in Experimental Cerebral Malaria: Modulation by Anticytokine Antibodies and Possible Role in Hypergammaglobulinemia", *J. Exp. Med.*, 172:1505–1508 (1990).

Hannum et al., "Interleukin–1 Receptor Antagonist Activity of a Human Interleukin–1 Inhibitor", *Nature*, 343:336–340 (1990).

Heinrich et al., "Interleukin–6 and the Acute Phase Response", *Biochem J.*, 265:621–636 (1990).

Helle et al., "Functional discrimination between interleukin 6 and interleukin 1", *Eur. J. Immunol.*, 18:1535–1540 (1988).

Helle et al., "Sensitive ELISA for interleukin–6: Detection of IL–6 in biological fluids: synovial fluids and sera", *J. Immunol. Methods*, 138:47–56 (1991).

Hess et al., "Cooperation of Glycolytic Enzymes", *J. Adv. Enzyme Req.*, 7:149–167 (1968).

Hibi et al., "Molecular Cloning and Expression of an IL–6 Signal Transducer, gp130", *Cell*, 63:1149–1157 (1990).

Hirano et al., "Biological and clinical aspects of interleukin 6", *Immunol. Today*, 11:443–449 (1990).

Hitzeman et al., "Isolation & Characterization of the Yeast 3–Phosphoglycerokinase Gene (PGK) by an Immunological Screening Technique", *J. Biol. Chem.*, 255(24):12073–12080 (1980).

Ho et al., "Site–directed mutagenesis by overlap extension using the polymerase chain reaction", *Gene*, 77:51–59 (1989).

Holland et al., "Isolation and Identification of Yeast Messenger Ribonucleic Acids Coding for Enolase, Glyceraldehyde–3–phosphate Dehydrogenase, and Phosphoglycerate Kinase", *Biochemistry*, 17:4900–4907 (1978).

Holland et al., "The Primary Structures of Two Yeast Enolase Genes", *J. Biol. Chem.*, 256(3):1385–1395 (1981).

Hsiao et al., "High–frequency transformation of yeast by plasmids containing the cloned yeast ARG4 gene", *Proc. Nat'l Acad. Sci.*, U.S.A. 76(8):3829–3833 (1979).

Ida et al., "Establishment of Strongly Neutralizing Monoclonal Antibody to Human Interleukin–6 and its Epitope Analysis", *Biochem. Biophys. Res. Commun.*, 165(2):728–734 (1989).

Jilka et al., "Increased Osteoclast Development After Estrogen Loss: Mediation by Interleukin–6", *Science*, 257:88–91 (1992).

Jourdan et al., "IFN–α Induces Autocrine Production of IL–6 in Myeloma Cell Lines", *J. Immunol.*, 147(2):4402–4407 (1991).

Klein et al., "Murine Anti–Interleukin–6 Monoclonal Antibody Therapy for a Patient With Plasma Cell Leukemia", *Blood*, 78(5):1198–1204 (1991).

Knauf et al., "Relationship of Effective Molecular Size to Systemic Clearance in Rats of Recombinant Interleukin–2 Chemically Modified with Water–soluble Polymers", *J. Biol. Chem.*, 263(29):15064–15070 (1988).

Krüttgen et al., "Structure–Function analysis of human interleukin–6", *FEBS Letters*, 262(2):323–326 (1990).

Krüttgen et al., "The three carboxy–terminal amino acids of human interleukin–6 are essential for its biological activity", *FEBS Letters*, 273(1,2):95–98 (1990).

Leebeek et al., "Identification of a Receptor Binding Site in the Carboxy Terminus of Human Interleukin–6", *J. Biol. Chem.*, 267:14832–14838 (1992).

Lütticken et al., "Evidence for the importance of a positive charge and an α–helical structure of the C–terminus for biological activity of human IL–6", *FEBS Letters*, 282(2):265–267 (1991).

Matteucci et al., "Synthesis of Deoxyoligonucleotides on a Polymer Support", *J. Am. Chem. Soc.*, 103:3185–3191 (1981).

Messing et al., "A system for shotgun DNA sequencing", *Nucl. Acids Res.*, 9(2):309–321 (1981).

Nishimura et al., "Role of leucine residues in the C–terminal region of human interleukin–6 in the biological activity", *FEBS*, 311:271–275 (1992).

Nishmura et al., "Site–specific mutagenesis of human interleukin–6 and its biological activity", *FEBS Lett.*, 281(1,2):167–169 (1991).

Nuijens et al., "Proteolytic Inactivation of Plasma C1 Inhibitor in Sepsis", *J. Clin. Invest.*, 84:443–450 (1989).

Pedersen et al., "Recombinant Human Extrinsic Pathway Inhibitor", *J. Biol. Chem.*, 265(28):16786–16793 (1990).

Poupart et al., "B cell growth modulating and differentiating activity of recombinant human 26–kd protein (BSF–2, HuIFN–$\beta_2$, HPGF)", *Embo. J.*, 6(5):1219–1224 (1987).

Roodman et al., "Interleukin 6", *J. Clin. Invest.*, 89:46–52 (1992).

Rose–John et al., "Structural and Functional Studies on the Human Interleukin–6 Receptor", *J. Biol. Chem.*, 266(6):3841–3846 (1991).

Sanger et al., "DNA sequencing with chain–terminating inhibitors", *Proc. Nat'l Acad. Sci., U.S.A.*, 74(12):5463–5467 (1977).

Sehgal, "Interleukin 6 in Infection and cancer", *Proc. Soc. Exp. Biol. Med.*, 195:183–191 (1990).

Shaw et al., "A general method for the transfer of cloned genes to plant cells", *Gene*, 23:315–330 (1983).

Shimatake et al., "Purified λ regulatory protein cII positively activates promoters for lysogenic development", *Nature*, 292:128–132 (1981).

Snouwaert et al., "Effects of Site–Specific Mutations on Biologic Activities of Recombinant Human IL–6", *J. Immunol.*, 146(2):585–591 (1991).

Snouwaert et al., "Role of Disulfide Bonds in Biologic Activity of Human Interleukin–6", *J. Biol. Chem.*, 266:23097–23102 (1991).

Starnes et al., "Anti–IL–6 Monoclonal Antibodies Protect Against Lethal *Escherichia coli* Infection and Lethal Tumor Necrosis Factor–α Challenge in Mice", *J. Immunol.*, 145(12):4185–4191 (1990).

Stinchcomb et al., "Isolation and characterisation of a yeast chromosomal replicator", *Nature*, 282:39–43 (1979).

Strassman et al., "Evidence for the Involvement of Interleukin 6 in Experimental Cancer Cachexia", *J. Clin. Invest.*, 89:1681–1684 (1992).

Studier et al., "Use of T7 RNA Polymerase to Direct Expression of Cloned Genes", *Meth. Ezjnymol,*, 185:60–89 (1990).

Taga et al., "Interleukin–6 Triggers the Association of Its Receptor with a Possible Signal Transducer, gp130", *Cell*, 58:573–581 (1989).

Taga et al., "Receptors for B Cell Stimulatory Factor 2", *J. Exp. Med.*, 166:967–981 (1987).

Tschumper et al., "Sequence of a yeast DNA fragment containing a chromosomal replicator and the TRP1 Gene", *Gene*, 10:157–166 (1980).

Van Snick, "Interleukin–6: An Overview", *Ann. Rev. Immunol.*, 8:253–278 (1990).

Van Solingen et al., "Fusion of Yeast Spheroplasts", *J. Bact.*, 130(2):946–947 (1977).

Ward et al., "Effect of pH and denaturants on the folding and stability of murine interleukin–6", *Protein Sci.*, 2(8):1291–1300 (1993).

Yamasaki et al., "Cloning and Expression of the Human Interleukin–6 (BSF–2/IFNβ 2) Receptor", *Science*, 241:825–828 (1988).

Yasueda et al., "Effect of Semi–Random Mutagenesis at the C–Terminal 4 Amino Acids of Human Interleukin–6 on its Biological Activity", *Biochem. Biophys. Res. Comm.*, 187(1):18–25 (1992).

Zhang et al., "Purification and characterization of a recombinant murine interleukin–6: isolation of N–and C–terminally truncated forms", *Eur. J. Biochem.*, 207:903–913 (1992).

Zuraw et al., "Regulation of the Hepatic Synthesis of C1 Inhibitor by the Hepatocyte Stimulating Factors Interleukin 6 and Interferon γ", *J. Biol. Chem.*, 265(21):12664–12670 (1990).

METHOD OF TREATING AN IL-6 RELATED DISEASE WITH INTERLEUKIN-6 RECEPTOR ANTAGONISTS

This is a Divisional of U.S. application Ser. No. 08/357,538, filed Dec. 16, 1994, now U.S. Pat. No. 5,591,827 which is a continuation of U.S. application Ser. No. 07/959,942, filed Oct. 20, 1992, now abandoned.

FIELD OF THE INVENTION

This invention is in the field of immunology and control of host defense mechanisms. More specifically, this invention relates to the discovery of a class of interleukin-6 muteins which interfere with the interaction between interleukin-6 and its two receptor proteins. This invention also relates to the use of such muteins to control and prevent interleukin-6 related diseases.

BACKGROUND OF THE INVENTION

Interleukin-6 (IL-6) is a multi-functional cytokine playing a central role in host defense mechanisms. Heinrich et al., *Biochem. J.* (1990) 265:621; Van Snick, J. *Annu. Rev. Immunol.* (1990)8:253; and Hirano et al., *Immunol. Today* (1990) 11:443. However, in a variety of human inflammatory, autoimmune, and neoplastic diseases, abnormal IL-6 production is observed and has been suggested to play a role in the pathogenesis of those diseases. Hirano et al., supra; Sehgal, P. B., *Proc. Soc. Exp. Biol. Med.* (1990) 195:183; Grau, G. E., *Eur. Cytokine Net* (1990) 1:203; Bauer et al., *Ann. Hematol.* (1991)62:203; Campbell et al., *J. Clin. Invest.* (1991) 7:739; and Roodman et al., *J. Clin. Invest.* (1992) 89:46. Inhibitors of IL-6 bioactivity might thus be useful to study its role in disease and could have broad therapeutic applications.

IL-6 overproduction is involved in sepsis (Starnes, Jr., H. F. et al., *J. Immunol.* (1990) 145:4185), and is also implicated in multiple myeloma disease, or plasma cell leukemia (Klein, B. et al., *Blood* (191) 78:1198). Other diseases include bone resorption (osteoporosis) (Roodman, G. D. et al., *J. Clin. Invest.* (1992) 89:46; Jilka, R. L. et al., *Science* (1992) 257:88–91), cachexia (Strassman, G. et al., *J. Clin. Invest.* (1992) 89:1681), psoriasis, mesangial proliferative glomerulonephritis, renal cell carcinoma, Kaposi's sarcoma, rheumatoid arthritis, hyper gammaglobulinemia (Grau, G. E. et al., *J. Exp. Med.* (1990) 172:1505), Castleman's disease, IgM gammapathy, cardiac myxoma and autoimmune insulin-dependent diabetes (Campbell, I. L. et al., *J. Clin. Invest.*, (1991) 87:739).

IL-6 functions through interaction with at least two specific receptors on the surface of target cells. Taga et al., *J. Exp. Med.* (1987) 166:967; and Coulie et al., *Eur. J. Immunol.* (1987) 17:1435. The cDNAs for these two receptor chains have been cloned, and they code for two transmembrane glycoproteins: the 80 kDa IL-6 receptor ("IL-6R") and a 130 kDa glycoprotein called "gp130". Yamasaki et al., *Science* (1988) 241:825; and Hibi et al., *Cell* (1990) 63:1149. IL-6 interacts with these glycoproteins following a unique mechanism. First, IL-6R binds to IL-6 with low affinity (Kd=about 1 nM) without triggering a signal. Taga et al., *Cell* (1989) 58:573. The IL-6/IL-6R complex subsequently associates with gp130, which transduces the signal. Hibi et al., supra; and Taga et al., supra. Gp130 itself has no affinity for IL-6 in solution, but stabilizes the IL-6 /IL-6 R complex on the membrane, resulting in high affinity binding of IL-6 (Kd=about 10 pM). Hibi et al., supra. It was recently found that gp130 is also a low affinity receptor for oncostatin M and an affinity converter for the LIF receptor (Gearing, D. P. et al., *Science* (1992) 255:1434).

Mature human (h) IL-6 is a 185 amino acid polypeptide containing two disulfide bonds ($Cys_{45}$ to $Cys_{51}$ and $Cys_{74}$ to $Cys_{84}$). Clogston et al., *Arch. Biochem. Biophys.* (1989) 272:144. The first 28 residues can be deleted without affecting bioactivity. Brakenhoff et al., *J. Immunol.* (1989) 143:1175. Bioactivity of hIL-6 appears to be conformation dependent. Large internal deletions disrupt the overall structure of the molecule and completely abolish activity. Snouwaert et al., *J. Immunol.* (1991) 146:585; and Fontaine et al., *Gene* (1991) 104:227. Maintenance of the second (but not the first) disulfide bond is critical, especially in bioassays involving human cell lines. Snouwaert et al., *J. Biol. Chem.* (1991) 266:23097. Regions critical to activity comprise residues $Ile_{30}$ to $Asp_{35}$ (see Brakenhoff et al., supra; Fontaine et al., supra; and Arcone et al., *FEBS Letters* (1991) 288:197), $Ala_{154}$ to $Thr_{164}$ (see Ida et al., *Biochem, Biophys. Res. Commun.* (1991) 165:728; and Nishimura et al., *FEBS Letters* (1991) 281:167) and $Arg_{183}$ to $Met_{183}$ (see Kruttgen et al., *FEBS Letters* (1990) 262:323; Brakenhoff et al., *J. Immunol.* (1990) 145:561; and Kruttgen et al., *FEBS Letters* (1990) 273:95). Substitution analysis of individual residues have implicated $Leu_{159}$, $Met_{162}$ and $Leu_{166}$ to be important both for activity and binding to IL-6R (see Nishimura et al., supra). A positive charge and α-helical C-terminal structure were found to be essential for activity. Lütticken et al., *FEBS Letters* (1991) 282:265.

One method for neutralization of IL-6 activity is the use of antibodies to IL-6. Neutralizing monoclonal antibodies (MAbs) to IL-6 can be divided in two groups, based on the recognition of two distinct epitopes on the IL-6 molecule, designated Site I and Site II. Site I is a conformational epitope composed of both amino terminal and carboxy terminal portions of the IL-6 molecule: the amino terminal portion includes amino acids $Ile_{30}$-$Asp_{35}$, while the carboxy terminal portion includes critical amino acids $Arg_{183}$-$Met_{185}$. Site II includes critical amino acids $Ala_{154}$-$Thr_{163}$. Brakenhoff et al. (1990), supra.

Another way to neutralize IL-6 activity is to inhibit the ligand-receptor interactions with specific receptor-antagonists. The feasibility of this general type of approach was recently demonstrated with a natural occurring receptor antagonist for interleukin-1. Hannum, C. H. et al., *Nature* (1990) 343:336–340. However, no natural receptor-antagonist has been identified for IL-6 so far. Nor has any hIL-6 variant with antagonistic properties been discovered. This invention uses the information gleaned from the Site I and Site II work with MAbs to construct hIL-6 variants that act as IL-6 receptor antagonists.

SUMMARY OF THE INVENTION

This invention relates to the discovery of a role for site I in IL-6 binding to IL-6R and for site II in IL-6/gp130 interaction. According to the IL-6 receptor model, IL-6 variants that bind normally to IL-6R, and whose subsequently formed IL-6 variant/IL-6R complex fails to interact with gp130, will function as receptor-antagonists. The inventors herein have analyzed substitution mutants in the Site II region for residual bioactivity in various IL-6 bioassays. One of the isolated mutants showed a 1,000 to 10,000-fold reduction in specific activity in assays with human cells, and could specifically antagonize the activity of wild-type recombinant (r) hIL-6 in two of three human assays.

It is accordingly a primary object of the present invention to provide a newly identified class of molecules that are antagonists of IL-6 as newly discovered agents.

It is a further object of this invention to provide oligonucleotide sequences encoding IL-6 receptor antagonists.

It is another object of this invention to provide pharmaceutical compositions for the treatment of IL-6 related diseases, especially sepsis and multiple myeloma.

Accordingly, in one aspect of this invention, a group of IL-6 receptor antagonist molecules are provided. In a preferred embodiment, the IL-6 receptor antagonists are IL-6 molecules containing one or more site II mutations.

In another aspect of this invention, pharmaceutical compositions are provided comprising an IL-6 receptor antagonist and a pharmaceutically acceptable carrier.

In a further aspect of this invention, a method for treating IL-6 related diseases is provided, said method comprising administering to a patient in need of such treatment a pharmaceutical composition containing an amount of an IL-6 receptor antagonist effective for treating sepsis and a pharmaceutically acceptable carrier. In preferred embodiments, the IL-6 related disease is sepsis or multiple myeloma.

BRIEF DESCRIPTION OF THE DRAWINGS

FIG. 2 shows the dose response curve of wild type IL-6 and two IL-6 mutants in various assays with human cell lines. (A) shows the amount of IgG1 synthesis by CESS cells; (B) shows the amount of C1 esterase inhibitor production by HepG2 cells; and (C) shows the amount of tritiated thymidine incorporated by human myeloma cell line XG-1.

FIG. 3 shows the inhibition of recombinant human IL-6 $Q_{160}E$, $T_{163}P$ on wild type IL-6 activity in (A) the CESS assay; and (B) the HepG2 assay.

DETAILED DESCRIPTION OF THE INVENTION

The invention described herein draws on previously published work and pending patent applications. By way of example, such work consists of scientific papers, patents or pending patent applications. All of these publications and applications, cited previously or below are hereby incorporated by reference. Although any similar or equivalent methods and materials may be employed in the practice or testing of the present invention, the preferred methods and materials are now described.

Definitions

The term "interleukin 6" or "IL-6", as used herein refers to IL-6 and to fragments, deletions, additions, substitutions, mutations and modifications thereof which retain the biological characteristics of the natural IL-6. Unless otherwise specified, the term refers to human IL-6.

The term "IL-6 related diseases" as used herein, refers to diseases associated with IL-6 overproduction including sepsis, multiple myeloma disease (plasma cell leukemia), bone resorption (osteoporosis), cachexia, psoriasis, mesangial proliferative glomerulonephritis, renal cell carcinoma, Kaposi's sarcoma, rheumatoid arthritis, hypergammaglobulinemia, Castleman's disease, IgM gammopathy, cardiac myxoma and autoimmune diabetes.

The term "IL-6 receptor antagonist", as used herein refers to molecules that interfere with the normal functioning of IL-6, as determined by specific inhibition of the wild type IL-6 molecule in in vitro bioassays, such as: (1) inhibition of IL-6 induction of production of acute phase proteins; (2) inhibition of IL-6 induction of myeloma or plasmacytoma growth; and (3) inhibition of IL-6 induction of immunoglobulin synthesis by human B cells. When the particular IL-6 receptor antagonist is a polypeptide of determined sequence, this invention also contemplates the term to include fragments, deletions, additions, substitutions, mutations and modifications thereof which retain the biological characteristics of the determined polypeptide.

A "mutation" in a protein alters its primary structure due to changes in the nucleotide sequence of the DNA which encodes it. These mutations include allelic variants. A "modified" protein differs from the unmodified protein as a result of post-translational events which change the glycosylation or lipidation pattern, or the primary, secondary, or tertiary structure of the protein. Changes in the primary structure of a protein can also result from deletions, additions, or substitutions. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral and polar, or neutral and nonpolar. Furthermore, three of the encoded amino acids are aromatic. It is generally preferred that encoded peptides differing from the determined IL-6 receptor antagonist contain substituted codons for amino acids which are from the same group as that of the amino acid replaced. Thus, in general, the basic amino acids Lys, Arg, and His are interchangeable; the acidic amino acids Asp and Glu are interchangeable; the neutral polar amino acids Ser, Thr, Cys, Gln, and Asn are interchangeable; the nonpolar aliphatic amino acids Gly, Ala, Val, Ile, and Leu are conservative with respect to each other (but because of size, Gly and Ala are more closely related and Val, Ile and Leu are more closely related), and the aromatic amino acids Phe, Trp and Tyr are interchangeable.

It should further be noted that if IL-6 receptor antagonist polypeptides are made synthetically, substitutions by amino acids which are not naturally encoded by DNA may also be made. For example, alternative residues include the omega amino acids of the formula $NH_2(CH_2)_nCOOH$ wherein n is 2–6. These are neutral, nonpolar amino acids, as are sarcosine, t-butyl alanine, t-butyl glycine, N-methyl isoleucine, and norleucine. Phenylglycine may substitute for Trp, Tyr or Phe; citrulline and methionine sulfoxide are neutral polar, cyclohexylalanine is neutral nonpolar, cysteic acid is acidic, and ornithine is basic. Proline may be substituted with hydroxyproline and retain the conformation conferring properties.

The "biological characteristics" of a protein refers to the structural or biochemical function of the protein in the biological process of the organism in which it participates. Examples of biological characteristics of IL-6 receptor antagonists include: (1) inhibition of $IgG_1$ synthesis by CESS cells induced by wild type IL-6; (2) induction of C1 esterase inhibitor synthesis by HepG2 cells induced by wild type IL-6 ; (3) ability to bind to the IL-6 receptor without activity on IL-6-responsive cells; (4) competition with wild type IL-6 for binding to the IL-6 receptor; and (5) inhibition of biological activity of wild type IL-6 on target cells.

As used herein, "Site I" refers to a conformational epitope on the IL-6 molecule recognized by the monoclonal antibody MAb CLB.IL-6/8. The epitope includes sites at both the amino terminal and carboxy terminal portions of the IL-6 molecule: the amino terminal portion includes amino acids $Ile_{30}$-$Asp_{35}$; while the carboxy terminal portion includes critical amino acids $Arg_{183}$-$Met_{185}$. "Site II" includes critical amino acids $Ala_{154}$-$Thr_{163}$, and other regions corresponding to the conformational epitope on the IL-6 molecule recognized by the monoclonal antibody MAb CLB.IL-6/16.

Preparation of IL-6 Receptor Antagonists

IL-6 receptor antagonists may be produced synthetically by the method of Merrifield et al. IL-6 receptor antagonists may be produced recombinantly as shown in U.S. Pat. No. 4,966,852. For example, the cDNA for the protein can be incorporated into a plasmid for expression in prokaryotes or eukaryotes. U.S. Pat. No. 4,847,201 ,which is hereby incorporated by reference in its entirety, provides details for transforming microorganisms with specific DNA sequences and expressing them. There are many other references known to those of ordinary skill in the art which provide details on expression of proteins using microorganisms. Many of those are cited in U.S. Pat. No. 4,847,201, such as Sambrook, J. et al., *Molecular Cloning*, Cold Spring Harbor Press (2d ed. 1989).

The following is an overview about transforming and expressing IL-6 receptor antagonists in microorganisms. IL-6 receptor antagonists DNA sequences may be incorporated into plasmids, such as pUNC13 or pBR3822, which are commercially available from companies such as Boehringer-Mannheim. Once the IL-6 receptor antagonist DNA is inserted into a vector, it can be cloned into a suitable host. The DNA can be amplified by techniques such as those shown in U.S. Pat. No. 4,683,202 to Mullis and U.S. Pat. No. 4,683,195 to Mullis et al. After the expression vector is transformed into a host such as *E. coli* the bacteria may be fermented and the protein expressed. Bacteria are preferred prokaryotic microorganisms and *E. coli* is especially preferred. A preferred microorganism useful in the present invention is *E. coli* K-12, strain MM294 deposited with the ATCC on Feb. 14, 1984, under the provisions of the Budapest Treaty, Accession Number 39607. Alternatively, IL-6 receptor antagonists may be introduced into mammalian cells. These mammalian cells may include CHO, COS, C127, HepG2, SK Hep, baculovirus, and infected insect cells (see also U.S. Pat. No. 4,847,201, referred to above). See also Pedersen et al., *J. Biol. Chem.* (1990) 265:16786–16793.

Some specific details about the production of a recombinant protein typically involves the following:
Suitable Hosts, Control Systems and Methods First, a DNA encoding the mature protein (used here to include all muteins); the preprotein; or a fusion of the IL-6 receptor antagonist protein to an additional sequence which does not destroy its activity or to additional sequence cleaved under controlled conditions (such as treatment with peptidase) to give an active protein, is obtained. If the sequence is uninterrupted by introns it is suitable for expression in any host. If there are introns, expression is obtainable in mammalian or other eucaryotic systems capable of processing them. This sequence should be in excisable and recoverable form. The excised or recovered coding sequence is then placed in operable linkage with suitable control sequences in a replicable expression vector. The vector is used to transform a suitable host and the transformed host cultured under favorable conditions to effect the production of the recombinant IL-6 receptor antagonists.

Genomic or cDNA fragments are obtained and used directly in appropriate hosts. The constructions for expression vectors operable in a variety of hosts are made using appropriate replications and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, or mammalian cells are presently useful as hosts. Host systems which are capable of proper post-translational processing are preferred. Accordingly, although procaryotic hosts are in general the most efficient and convenient for the production of recombinant proteins, eucaryotic cells, and, in particular, mammalian cells are preferred for their processing capacity, for example, the ability to form the proper glycosylation patterns. In addition, there is more assurance that the native signal sequence will be recognized by the mammalian host cell, thus making secretion possible, and purification thereby easier.

Control Sequences and Corresponding Hosts

Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al., *Gene* (1977) 2:95. pBR322 contains genes for ampicillin and tetracycline resistance, and thus provides additional markers which can be either retained or destroyed in constructing the desired vector. Commonly used procaryotic control sequences are defined herein to include promoters for transcription initiation, optionally with an operator, along with ribosome binding site sequences, which include such commonly used promoters as the beta-lactamase (penicillinase) and lactose (lac) promoter systems (Chang, et al., *Nature* (1977) 198:1056); the tryptophan (trp) promoter system (Goeddel, et al., *Nucleic Acids Res.* (1980) 8:4057); the T7 promoter (Studier, F. W. et al., *Meth. Enzymol.* (1990) 185:60); and the λ derived $P_L$ promoter and N-gene ribosome binding site (Shimatake, et al., *Nature* (1981) 292:128), which has been made useful as a portable control cassette, as set forth in U.S. Pat. No. 4,711,845, issued Dec. 8, 1987. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used although a number of other strains are commonly available. Examples of plasmid vectors suitable for yeast expression are shown in Broach, J. R., *Meth. Enz.* (1983) 101:307; Stinchcomb et al., *Nature* (1979) 282:39; and Tschempe et al., *Gene* (1980) 10:157 and Clarke, L., et al., *Meth. Enz.* (1983) 101:300. Control sequences for yeast vectors include promoters for the synthesis of glycolytic enzymes (Hess, et al., *J. Adv. Enzyme Reg.* (1968) 7:149; Holland, et al., *Biochemistry* (1978) 17:4900). Additional promoters known in the art include the promoter for 3-phosphoglycerate kinase (Hitzeman, et al., *J. Biol. Chem.* (1980) 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, supra). It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J. et al., *J. Biol. Chem.* (1981) 256:1385) or the LEU2 gene obtained from YEp13 (Broach, J. et al., *Gene* (1978) 8:121), however, any vector containing a yeast compatible promoter, origin of replication and other control sequences is suitable.

It is also, of course, possible to express genes encoding polypeptides in eucaryotic host cell cultures derived from multicellular organisms. See, for example, *Tissue Culture*, 1973, Cruz and Patterson, eds., Academic Press. Useful host cell lines include murine myelomas N51, VERO, HeLa cells, Chinese hamster ovary (CHO) cells, COS, C127, Hep G2, SK Hep, baculovirus, and infected insect cells. Expression vectors for such cells ordinarily include promoters and control sequences compatible with mammalian cells such as, for example, the commonly used early and later promoters from Simian Virus 40 (SV40) (Fiers, et al., *Nature* (1978) 273:113), or other viral promoters such as those derived from polyoma, Adenovirus 2, bovine papilloma virus, or avian sarcoma viruses, or immunoglobulin promoters and heat shock promoters. General aspects of mammalian cell host system transformations have been described by Axel, U.S. Pat. No. 4,399,216, issued Aug. 16, 1983. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryates. Plant cells are also now available as hosts, and control sequences compatible with plant cells such as the nopaline synthase promoter and polyadenylation signal sequences (Depicker, A., et al., *J. Mol. Appl. Gen.* (1982) 1:561) are available. Methods and vectors for transformation of plant cells have been disclosed in PCT Publication No. WO 85/04899, published Nov. 7, 1985.

Host strains useful in cloning and expression herein are as follows:

For cloning and sequencing, and for expression of construction under control of most bacterial promoters, *E. coli* strain MM294 obtained from *E. coli* Genetic Stock Center GCSC #6135. For expression under control of the $P_L N_{RBS}$ promoter, *E. coli* strain K12 MC1000 lambda lysogen, $N_7N_{53}cI857$ SusP80, a strain deposited with the American Type Culture Collection (ATCC 39531), may be used. *E. coli* DG116, which was deposited with the ATCC (Accession No. 53606) on Apr. 7, 1987, may also be used.

For M13 phage recombinants, *E. coli* strains susceptible to phage infection, such as *E. coli* K12 strain DG98, can be employed. The DG98 strain has been deposited with the ATCC (ATCC 39768) on Jul. 13, 1984.

Mammalian expression can be accomplished in COS-A2 cells, COS-7, CV-1, murine myelomas N51, VERO, HeLa cells, Chinese hamster ovary (CHO) cells, COS, C127, Hep G2, SK Hep, baculovirus, and infected insect cells. Insect cell-based expression can be in *Spodoptera frugiperda*.

Transformations

Depending on the host cell used, transformation is done using standard techniques appropriate to such cells. The calcium treatment employing calcium chloride, as described by Cohen, S. N., *PNAS* (USA) (1972) 69:2110, is used for procaryotes or other cells which contain substantial cell wall barriers. Infection with *Agrobacterium tumefaciens* (Shaw, C. H. et al., *Gene* (1983) 23:315) is used for certain plant cells. For mammalian cells without such cell walls, the calcium phosphate precipitation method of Graham and van der Eb. *Virology* (1987) 52:546 is preferred. Transformations into yeast are carried out according to the method of Van Solingen, P. et al., *J. Bact.* (1977) 130:946 and Hsiao, C. L. et al., *PNAS* (USA) (1979) 76:3829.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequehce is cleaved by 1 unit of enzyme in about 20 μl of buffer solution; in the examples herein, typically, an excess of restriction enzyme is used to insure complete digestion of the DNA substrate. Incubation times of about 1 hour to 2 hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods of Enzymology*. 1980, 65:499–560.

Synthetic oligonucleotides may be prepared by the triester method of Matteucci et al., *J. Am. Chem. Soc.* (1981) 103:3185–3191, or using automated synthesis methods. Kinasing of single strands prior to annealing or for labelling is achieved using an excess, e.g., approximately 10 units of polynucleotide kinase to 1 nmole substrate in the presence of 50 mM Tris, pH 7.6, 10 mM $MgCl_2$, 5 mM DTT, 1–2 mM ATP. If kinasing is for labelling of probe, the ATP will contain high specific activity $\gamma$-$^{32}$P.

Ligations are performed in 15–30 μl volumes under the following standard conditions and temperatures: 20 mM Tris-Cl pH 7.5, 10 mM $MgCl_2$, 10 mM DTT, 33 μg/ml bovine serum albumin (BSA), 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration.

In the vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^{2+}$ and $Mg^{2+}$ using about 1 unit of BAP per μg of vector at 60° C. for about 1 hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Modification of DNA Sequences

For portions of vectors derived from cDNA or genomic DNA which require sequence modifications, site specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form: 50% will have the original sequence. The plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Verification of Construction

Correct ligations for plasmid construction could be confirmed by first transforming E. coli strain MM294, or other suitable host, with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B. et al., PNAS (USA) (1969)62:1159, optionally following chloramphenicol amplification (Clewell, D. B., J. Bacteriol (1972) 110:667). The isolated DNA is analyzed by restriction and/or sequenced by the dideoxy method of Sanger, F., et al., PNAS (USA) (1977) 74:5463 as further described by Messing et al., Nucleic Acids Res. (1981) 9:309, or by the method of Maxam et al., Methods in Enzymology (1980) 65:499.

Purification of IL-6 Receptor Antagonists

IL-6 receptor antagonists may be produced in bacteria, such as E. coli, and subsequently purified. Generally, the procedures shown in U.S. Pat. Nos. 4,511,502; 4,620,948; 4,929,700; 4,530,787; 4,569,790; 4,572,798; and 4,748,234 can be employed. These patents are hereby incorporated by reference in their entireties. Typically, the heterologous protein (i.e., IL-6 receptor antagonist) is produced in a refractile body within the bacteria. To recover and purify the protein, the cells are lysed and the refractile bodies are centrifuged to separate them from the cellular debris (see U.S. Pat. No. 4,748,234 for lowering the ionic strength of the medium to simplify the purification). Thereafter, the refractile bodies containing the IL-6 receptor antagonist are denatured, at least once (typically in a non-reducing environment), and the protein is oxidized and refolded in an appropriate buffer solution for an appropriate length of time. IL-6 receptor antagonists may be purified from the buffer solution by various chromatographic methods, such as those mentioned above for the mammalian cell derived IL-6 receptor antagonists. Preferably, IL-6 receptor antagonists are purified by affinity chromatography using, anti-IL-6 monoclonal antibodies. Additionally, the methods shown in U.S. Pat. No. 4,929,700 may be employed.

Formation and Administration

IL-6 receptor antagonists are administered at a concentration that is therapeutically effective to treat and prevent IL-6 related diseases, including sepsis and multiple myeloma. To accomplish this goal, IL-6 receptor antagonists are preferably administered intravenously. Methods to accomplish this administration are known to those of ordinary skill in the art.

Before administration to patients, formulants may be added to IL-6 receptor antagonists. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v% and 7.0 w/v%, more preferable between 2.0 and 6.0 w/v%. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP Nos. 270,799 and 268,110.

Additionally, IL-6 receptor antagonists can be chemically modified by covalent conjugation to a polymer to increase its circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and has the general formula: R(O—CH$_2$—CH$_2$)$_n$O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/IL-6 receptor antagonist of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG/IL-2 conjugates is found in U.S. Pat. No. 4,766,106, both of which are hereby incorporated by reference in their entireties.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

Administration to Affected Individuals

As stated above, IL-6 receptor antagonists are useful to treat human patients with IL-6 related diseases, including sepsis and multiple myeloma. Generally, sepsis patients are characterized by high fever (>38.5° C.) or hypothermia (<35.5° C.), low blood pressure, tachypnea (>than 20 breaths/minute), tachycardia (>than 100 beats/minute), leukocytosis (>15,000 cells/mm$^3$) and thrombocytopenia (<than 100,000 platelets/mm$^3$) in association with bacteremia. IL-6 receptor antagonists are to be administered as soon as a patient is suspected of being septic; presenting themselves with a >20% drop in fibrinogen or appearance of fibrin split products, a rise in the patient's temperature and the diagnosis of leukopenia and hypotension associated with sepsis. As also stated above, the preferred route is by intravenous administration. Generally, IL-6 receptor antagonists are given at a dose between 1 µg/kg and 20 mg/kg, more preferably between 20 µg/kg and 10 mg/kg, most preferably between 1 and 7 mg/kg. Preferably, it is given as a bolus dose, to increase circulating levels by 10–20 fold and for 4–6 hours after the bolus dose. Continuous infusion may also be used after the bolus dose. If so, IL-6 receptor antagonists may be infused at a dose between 5 and 20 µg/kg/minute, more preferably between 7 and 15 µg/kg/minute.

When used to treat sepsis, IL-6 receptor antagonists may be given in combination with other agents which would be effective to treat sepsis. For example, the following may be administered in combination with IL-6 receptor antagonists: antibiotics that can treat the underlying bacterial infection; monoclonal antibodies that are directed against bacterial cell wall components; receptors that can complex with cytokines that are involved in the sepsis pathway; antibodies to cell adhesion molecules such as LFA-1; and generally any agent or protein that can interact with cytokines or complement proteins in the sepsis pathway to reduce their effects and to attenuate sepsis or septic shock.

IL-6 receptor antagonists may also be administered in conjunction with other similar modulatory cytokines including LIF, oncostatin M, CNTF and IL-11.

Antibiotics that are useful in the present invention include those in the general category of: beta-lactam rings (penicillin), amino sugars in glycosidic linkage (amino glycosides), macrocyclic lactone rings (macrolides), polycyclic derivatives of napthacenecarboxamide (tetracyclines), nitrobenzene derivatives of dichloroacetic acid, peptides (bacitracin, gramicidin, and polymyxin), large rings with a conjugated double bond system (polyenes), sulfa drugs derived from sulfanilamide (sulfonamides), 5-nitro-2-furanyl groups (nitrofurans), quinolone carboxylic acids (nalidixic acid), and many others. Other antibiotics and more versions of the above specific antibiotics may be found in Encyclopedia of Chemical Technology, 3rd Edition, Kirk-Othymer (ed.), Vol. 2, pages 782–1036 (1978) and Vol. 3, pages 1–78, Zinsser, *MicroBiology*, 17th Edition W. Joklik et al. (Eds.) pages 235–277 (1980), or Dorland's Illustrated Medical Dictionary, 27th Edition, W.B. Saunders Company (1988).

Monoclonal antibodies that may be administered along with IL-6 receptor antagonists include those found in PCT WO 88/03211, to Larrick et al., entitled Gram-Negative Bacterial Endotoxin Blocking Monoclonal Antibodies, and U.S. Ser. No. 07/876,854, filed Apr. 30, 1992, to Larrick et al. Both applications disclose specific monoclonal antibodies that are useful to treat sepsis and which bind to various antigens on the *E. coli* bacterial cell wall. A specifically preferred monoclonal antibody is that which is produced by hybridoma ATCC No. HB9431.

Other agents which may be combined with IL-6 receptor antagonists include monoclonal antibodies directed to cytokines involved in the sepsis pathway, such as those monoclonal antibodies directed to IL-6 or M-CSF, see U.S. Ser. No. 07/451,218, filed Dec. 15, 1989 to Creasey et al. and monoclonal antibodies directed to TNF, see Cerami et al., U.S. Pat. No. 4,603,106. Inhibitors of protein that cleave the mature TNF prohormone from the cell in which it was produced, see U.S. Ser. No. 07/395,253, filed Aug. 16, 1989, to Kriegler et al. Antagonists of IL-1, such as shown in U.S. Ser. No. 07/517,276, filed May 1, 1990 to Haskill et al. Inhibitors of IL-6 cytokine expression such as inhibin, such as shown in U.S. Ser. No. 07/494,624, filed Mar. 16, 1992, to Warren et al., and receptor based inhibitors of various cytokine such as IL-1. Antibodies to complement may also be employed.

Generally, IL-6 receptor antagonists may be useful for those diseases that occur due to the up-regulation of tissue factor brought on by TNF, IL-1 or other cytokines.

The present invention will now be illustrated by reference to the following examples which set forth particularly advantageous embodiments. However, it should be noted that these embodiments are illustrative and are not to be construed as restricting the invention in any way.

EXAMPLES

Materials and Methods

Antibodies and Cytokines

The production and purification of an IL-6 specific MAb has been described before in detail (see Brakenhoff et al. (1990)). The wild-type rIL-6 preparation used throughout these experiments as a standard is purified from *E. coli* carrying the HGF7 plasmid (see Brakenhoff et al., *J. Immunol.* (1987) 139:4116). HGF7 encodes an IL-6 fusion protein consisting of a 9 amino acid β-galactosidase derived leader followed by 4 glycines, an aspartic acid residue, and $Arg_{17}$-$Met_{185}$ of mature IL-6. Purification of HGF7 has been described before in Brakenhoff et al. (1990). Specific activity of purified rhIL-6 HGF7 as determined in the B9 assay is approximately $10^9$ U/mg. Recombinant IFN-γ was obtained from Genentech (San Francisco, Calif.).

Bacterial Strains and Vectors

Construction of the expression vector pUK-IL-6 is described in Brakenhoff et al., 1989. Expression of vectors occurred in an *E. coli* DH5α (GIBCO BRL) host.

EXAMPLE 1

Preparation of IL-6 Variants

A. Preparation of an IL-6 Variant Library

Random mutagenesis of the IL-6 region around $Trp_{158}$ was performed to identify residues which might be important to the biological activity of IL-6. The vector pUK-IL-6 was used for construction of the library of rhIL-6 mutants with random substitutions in residues $Gln_{153}$-$Thr_{163}$. Restriction fragments with the desired substitutions suitable for subcloning in pUK-IL-6, were obtained in two steps by overlap extension PCR (see Ho et al., *Gene* (1989) 77:51). In the first PCR reactions, pUK-IL-6 was used as template. Fragment 1, running from the unique XbaI site in the IL-6 coding region, to amino acid $Thr_{163}$, was generated by combining a 5' primer (A) with (SEQ ID NO: 1) (nucleotides (nts) 477–498 of IL-6 coding region (see Brakenhoff et al., 1987, supra), and a 3' primer (B) with (SEQ ID NO: 2) (nts 537–570, corresponding to residues $Gln_{153}$-$Thr_{163}$). To obtain randomly distributed substitutions in primer B a similar approach was used as described by Derbyshire et al., *Gene* (1986) 46:145. Instead of contaminating each nucleotide reservoir with the three other monomers, the fifth channel of the oligo synthesizer (Applied Biosystems type 381A, Warrington, UK) was used during oligo synthesis: during each synthesis step both the channel containing 100 mM of the wild-type nucleotide and the fifth channel containing 1.25 mM of each of the four dNTP's were mixed in 1:1 ratio. With an oligo length of 34 this results in approximately 36% single, 36% multiple, and 28% no mutations per oligo. Fragment 2, running from $Gln_{153}$ to the BanII site, was generated by using a 5' primer (C) complementary to primer B (SEQ ID NO: 3) (nts 538–571) synthesized in the same manner as primer B. This oligo was combined with a 3' primer D, (SEQ ID NO: 4) (nts 609–629). PCRs were carried out with Taq polymerase as specified by the manufacturer (Perkin Elmer Cetus) by using 10 ng of template DNA and 100 ng of each primer (annealing 2 minutes at 50° C., extension 2.5 minutes at 65° C., denaturation 1.5 minutes at 95° C.; 30 cycles). After the first PCR reactions, fragments 1 and 2 were purified from low melting agarose and approximately 100 ng of each served as template in the second PCR reaction with primers A and D. After phenol/CHCl₃ extraction the second PCR product was digested with XbaI and BanII, gel purified and subcloned in XbaI-BanII digested pUK-IL-6. Following transformation to *E. coli* DH5α approximately 1,000 colonies were obtained. DNA manipulation procedures were performed as described in Brakenhoff et al., 1989 and Brakenhoff et al., 1990. Nucleotide sequences of selected mutants (see below) were obtained with cDNA derived oligonucleotide primers on dsDNA by using the "Sequenase" kit (United States Biochemical Corporation, Cleveland, Ohio).

B. Preparation and Screening of IL-6 Variants

Variants were subsequently selected for binding to a site I specific MAb (MAb CLB.IL-6/8) and loss of binding to a site II specific MAb (MAb CLB.IL-6/16) in ELISAs and the nucleotide sequence of plasmids encoding mutants with this phenotype was determined. 400 ampicillin resistant colonies were toothpicked in wells of 96-well flat bottom microtiterplates (NUNC) containing 100 μl LC amp medium (10 g of bactotryptone, 5 g of yeast extract, 8 g of NaCl, and 2 ml of Tris base per liter supplemented with 100 μg/ml final concentration of ampicillin). Following overnight culture at 37° C., bacteria were lysed by addition of lysozyme to 1 mg/ml and further incubation for 30 minutes at 37° C. 1 in 10 dilutions of the crude extracts in phosphate-buffered saline (PBS), 0.02% Tween-20, 0.2% gelatin were directly tested for reactivity in sandwich ELISAs with MAb CLB.IL-6/8 or 16 coated to the plastic and biotinylated polyclonal goat anti-rhIL-6 as detecting antibody. Bound polyclonal anti-rhIL-6 was detected with horseradish peroxidase conjugated streptavidin (Amersham, Amersham UK). Similarly prepared extracts of *E. coli* carrying pUK-IL-6 were used as positive control. Of the MAb CLB.IL-6/8 positive/MAb CLB.IL-6/16 negative mutants the nucleotide sequence of the XbaI-BanII fragment was subsequently determined. ELISA procedures and biotinylation of polyclonal antibodies have been described in detail by Brakenhoff et al., 1990, supra and Helle et al., *J. Immunol. Methods* (1991) 138:47.

As shown in Table 1, the MAb CLB.IL-6/16 epitope is disrupted by single substitution of $Gln_{155}$, $Asn_{156}$, $Trp_{158}$, and $Thr_{163}$. The double and triple substitution mutants suggest that residues $Ala_{154}$, $Leu_{159}$, $Gln_{160}$ and $Met_{162}$ might also be important for the MAb CLB.IL-6/16 epitope.

TABLE 1

Bioactivity of rhIL-6 mutants that do not bind to MAb CLB.IL-6/16

| IL-6 Variant | B9 Assay (U/μg)[a] | CESS Assay (U/μg)[a] |
|---|---|---|
| mature rhIL-6 | $6 \times 10^6$ | $1 \times 10^4$ |
| $Gln_{155}$His | $5 \times 10^6$ | $3 \times 10^4$ |
| $Asn_{156}$Lys | $1 \times 10^6$ | $6 \times 10^4$ |
| $Trp_{158}$*(Gln) | $5 \times 10^5$ | $4 \times 10^2$ |
| $Trp_{158}$Gly | $4 \times 10^6$ | $4 \times 10^3$ |
| $Trp_{158}$Arg | $1 \times 10^6$ | $5 \times 10^3$ |
| $Thr_{163}$Pro | $2 \times 10^6$ | <20 |
| $Ala_{154}$Glu, $Gln_{160}$His | $5 \times 10^5$ | not detectable |
| $Gln_{155}$His, $Gln_{157}$Pro | $6 \times 10^6$ | $2 \times 10^3$ |
| $Trp_{158}$Cys, $Met_{162}$Ile | $6 \times 10^4$ | $<10^4$ |
| $Trp_{158}$Arg, $Ser_{170}$Asn | $5 \times 10^6$ | $2 \times 10^3$ |
| $Gln_{160}$Glu, $Thr_{163}$Pro | $3 \times 10^6$ | <20 |
| $Ile_{137}$Leu, $Leu_{159}$Arg, $Met_{162}$Ile | $1 \times 10^7$ | $5 \times 10^3$ |

[a]Concentration and biological activity in B9 and CESS assay of SDS-extracts of rhIL-6 mutants that bound to MAb CLB.IL-6/8 but not to MAb CLB.IL-6/16 were measured as described above. 1 unit is the amount of variant giving half-maximal stimulation in each assay. Values derived from one of two assays are shown.

C. Bioactivity of IL-6 Mutants

The biological activity of crude extracts of various mutant proteins was subsequently measured both in the B9 assay and on IgG1 production by CESS cells. The B9 assay measures the murine hybridoma growth factor activity of rhIL-6 and variants as described in Aarden et al., *Eur. J. Immunol.* (1987) 17:1411 and Helle et al., *Eur. J. Immunol.* (1988) 18:1535. The CESS assay measures B-cell stimulatory factor-2 activity of rhIL-6 variants essentially as described by Poupart et al., *EMBO J.* (1987) 6:1219. Briefly, CESS cells ($6 \times 10^3$ cells/200 µl well in 96-well flat-bottom microtiterplates, in IMDM-5% .FCS-Trf) were incubated for 4 days with serial dilutions of rhIL-6 or rhIL-6 variant containing samples in triplicate. IL-6 induced IgG1 production by the cells was subsequently measured in a sandwich ELISA by using a mouse MAb specific for human IgG1 (MH161-1 M, Department of Immune Reagents, CLB, Amsterdam, The Netherlands) in combination with a horseradish peroxidase conjugated murine MAb specific for human IgG (MH16-1 ME, CLB) with a human serum as standard (H00-1234, CLB). ELISA procedures were as described above.

To measure the bioactivity of the MAb CLB.IL-6/8 positive/MAb CLB.IL-6/16 negative mutants, overnight cultures of *E. coli* DH5α carrying the mutant constructs were diluted 1:50 in 250 ml LC amp medium and subsequenfly cultured to an OD550 of 1.5. Bacteria were harvested by centrifugation, resuspended in 5 ml lysis buffer (PBS, 1% Tween-20, 10 mM EDTA, 2 mM PMSF) and lysed by sonication. To solubilize rhIL-6 containing inclusion bodies, SDS was subsequently added to 1%. After 1 hour incubation at room temperature, SDS-insoluble material was removed by centrifugation (15 minutes at 13,000 g).

Bioactivity of this SDS solubilized material was directly measured in the B9 and CESS assays starting from a 1/1000 dilution. The IL-6 variant concentration of these preparations was determined by means of a competitive inhibition radioimmunoassay (RIA) with IL-6 specific MAb CLB.IL-6/7 coupled to Sepharose 4B (Pharmacia LKB) and $^{125}$I-rhIL-6 HGF7, in the presence of 0.1% SDS. Unlabelled rhIL-6 HGF7, served as a standard. MAb CLB.IL-6/7 binds heat and SDS denatured IL-6 and recognizes IL-6 residues $Thr_{143}$-$Ala_{146}$ as determined by pepscan analysis (see Fontaine et al., *Gene* (1991) 104:227 and Arcone et al., *FEBS Letters* (1991) 288:197).

As shown in Table 1, all mutants were biologically active in the murine B9 hybridoma proliferation assay. However, although very active in the B9 assay, no activity could be detected for the rhIL-6 $Thr_{163}Pro$ (rhIL-6 $T_{163}P$) single-mutant and rhIL-6 $Gln_{160}Glu$, $Thr_{163}Pro$ (rhIL-6 $Q_{160}E$, $T_{163}P$) double-mutant preparation on human CESS cells. (The nomenclature $X_nY$ following a protein indicates that amino acid X at residue n has been replaced by amino acid Y, where X aid Y are the commonly used three-letter or one-letter abbreviations for the naturally-occurring amino acids.)

D. Expression and Purification of Two IL-6 Mutants

To confirm the role of the two mutants active in the B9 assay and inactive in the CESS assay described above, the IL-6 cDNA inserts from the vectors pUK-IL-6 $T_{163}P$ and pUK-IL-6 $Q_{160}E$, $T_{163}P$ were removed with NcoI and BamHI and subcloned in NcoI-BamHI digested pET8c. Plasmid DNA was prepared from *E. coli* DH5α carrying the pET8c constructs and transformed to *E. coli* BL21 (DE3). *E. coli* BL21 (DE3) carrying these expression plasmids were subsequently cultured to an OD550 of 0.6 in LC amp medium and expression was induced by addition of 0.5 mM IPTG (Sigma). After a 3 hour induction period, the bacteria were harvested by centrifugation and the IL-6 variants were purified essentially as described by Arcone et al., *Eur. J. Biochem.* (1991) 191:541, with some modifications. Briefly, following centrifugation, bacteria were resuspended in 1/20 of the culture volume 10 mM Tris-HCl pH 7.4, 2 mM PMSF and frozen at −20° C. Following thawing bacteria were lysed by sonication. The sonicate was then applied upon a sucrose cushion (40% sucrose, 10 mM Tris-HCl pH 7.4) and centrifuged for 1 hour at 47,000 g. Pelleted inclusion bodies were subsequently washed ones with PBS, 0.5% Tween-20, 10 mM EDTA, 2 mM PMSF and dissolved in 6M guanidine-HCl, 25 mM Tris-HClpH 7.4 (0.4 g wet weight/liter). Following two times dialysis against 20 volumes of 25 mM Tris-HCl pH 8.5, aggregates were removed by centrifugation for 1 hour at 11,000 g and the dialysate was concentrated 30-fold with an Amicon YM10 filtration unit (Amicon Corp., Danvers, Mass.). The concentrate was then directly applied on a fast Q Sepharose anion exchange column attached to a FPLC (Pharmacia LKB). Bound rhIL-6 variants were subsequently eluted with a linear gradient of NaCl in 25 mM Tris-HCl pH 8.5 and eluted at approximately 100 mM NaCl. The variants were subsequently sterile filtered and stored at −70° C. Protein concentration was determined both by measuring the optical density of the preparations and by the Bradford method (*Anal. Biochem.*, (1976) 72:248) using BSA as a standard. Bradford and $OD_{280}$ correlated best when assuming the $OD_{280}$ of a 10 mg/ml solution of IL-6 is 10.

Figure 1:
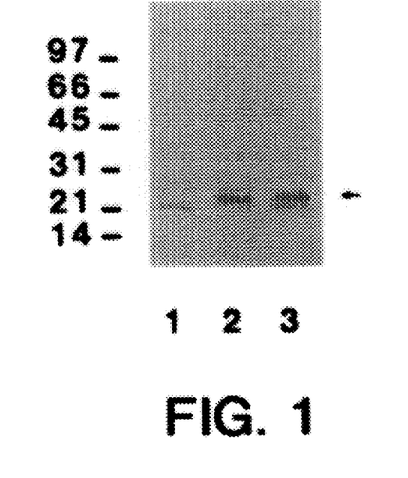
FIG. 1 shows a Coomassie blue-stained SDS-polyacrylamide gel of preparations of various IL-6 mutants. The lanes contain: (1) rhIL-6 HGF7; (2) rhIL-6 $T_{163}P$; (3) rhIL-6 $Q_{160}E$, $T_{163}P$. The arrow denotes the migration position of mature rhIL-6.

FIG. 1 shows a Coomassie blue stained SDS-polyacrylamide gel of the mutant preparations. The variants migrated with approximately the same molecular weight as mature rhIL-6. After the final purification step, two bands were observed in the rhIL-6 $Q_{160}E$, $T_{163}P$ preparation. Following Western blotting, both bands were recognized by an IL-6 specific MAb, suggesting that the lower band is a degradation product of the upper band (data not shown).

E. Bioactivity of Two IL-6 Mutants

The bioactivity of these two mutants were tested both in the CESS assay and in two other available bioassays for IL-6: the HepG2 assay and the XG-1 assay.

The HepG2 assay measures the hepatocyte stimulating activity of rhIL-6 variants through the induction of C1 esterase inhibitor (C1 inh.) production by HepG2 cells as described by Zuraw, B. L. et al., *J. Immunol.* (1990) 265:12664. Following culturing to confluency ($5 \times 10^5$ cells in 0.5 ml wells (Costar) in Iscove's Modified Dulbecco's Medium (IMDM) supplemented with 5% FCS, $5 \times 10^{-5}$ M 2-ME, penicillin (100 IU), streptomycin (100 µg/ml) and human transferrin (20 µg/ml; Behringwerke, Marburg, Germany) (IMDM-5% FCS-Trf), HepG2 cells were washed twice and stimulated with serial dilutions of rhIL-6 or rhIL-6 mutants for 48 hours in the same medium in duplicate. In some experiments, cells were washed again after 24 hours and the stimulus was repeated for 24 hours. This procedure results in a higher stimulation index. After the incubation period, C1 inh. synthesis was subsequently measured by sandwich RIA with anti-C1 inh. MAb RII coupled to Sepharose 4B and $^{125}$I-labelled sheep polyclonal anti-C1 inh. IgG with normal human plasma as a standard as described in Nuijens et al., *J. Clin. Invest.* (1989) 84:443 and Eldering et al., *J. Biol. Chem.* (1988)263:11776.

The XG-1 assay measures IL-6 activity on human myeloma cell line XG-1 essentially as described in Jourdan, M. et al., *J. Immunol.* (1991) 147:4402. Briefly, the cells were washed twice, incubated in IMDM-5% FCS-Trf for 4 hours at 37° C. and then washed again. $10^4$ cells/well in 200 µl IMDM-5% FCS-Trf in 96-well flat-bottom microtiterplates were subsequently incubated in triplicate with serial dilutions of rhIL-6 or rhIL-6 variants for 3 days. Following this culture period, proliferation of the cells was measured by labelling the cells with 7.4 kBq of [$^3$H]Thymidine (74

Gbq/mmol) for 4 hours and counting the radioactivity incorporated in the nuclei.

Figure 2A:
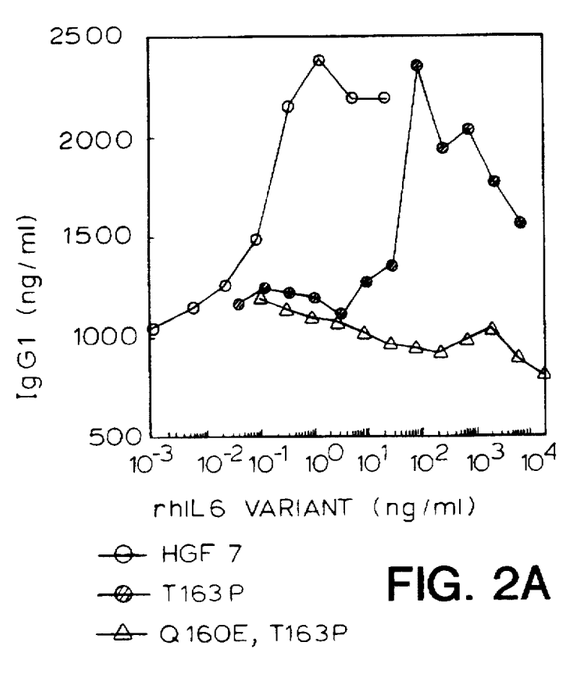
Figure 2B:
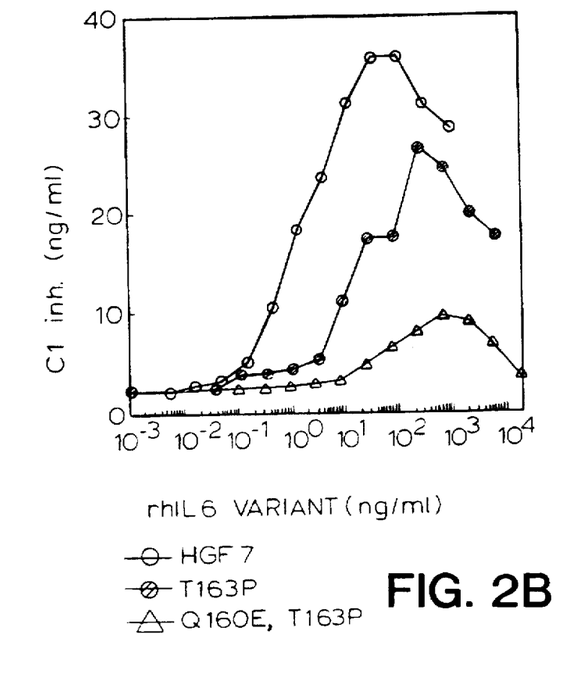
Figure 2C:
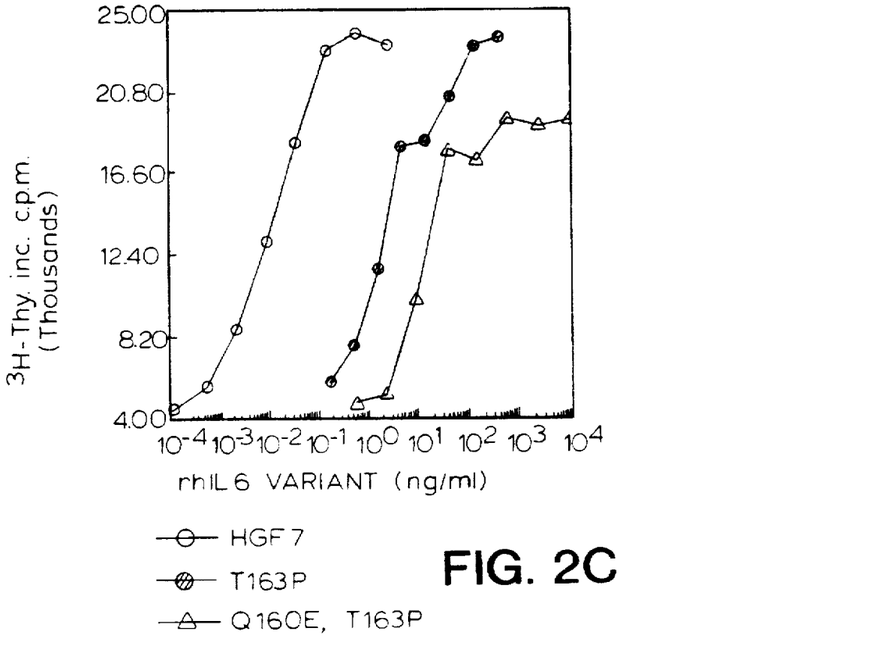

FIG. 2a–c shows representative dose response curves of the mutants in three different assays with human cell lines. In Table 2, the specific activities of the mutants in the human assays is depicted, together with the specific activities in the (murine) B9 assay, relative to that of wild-type rhIL-6 HGF7. In the experiment in FIG. 2a is shown that also the purified rhIL-6 $Q_{160}E$, $T_{163}P$ double-mutant did not induce IgG1 synthesis by the CESS cells. In some experiments however (see e.g. FIG. 3a), a small increase in background IgG1 production was observed. As shown in FIG. 2b, a weak induction of the acute phase protein C1 esterase inhibitor (C1 inh.) was reproducibly observed at high concentrations of the variant, with a strongly reduced plateau level as compared to wild-type rhIL-6 HGF7. However, although the specific activity of the double-mutant in inducing proliferation of the human myeloma cell line XG-1 (see Jourdan et al., supra and FIG. 2c) was approximately 1,000-fold reduced as compared to wild-type IL-6, almost the same plateau level was reached. On B9 cells the specific activity of rhIL-6 $Q_{160}E$, $T_{163}P$ was only 10-fold reduced (Table 2). RhIL-6 $T_{163}P$ was more active than the double-mutant in all assays, with a reduced plateau in CESS and HepG2 assays. The activity of the rhIL-6 $Q_{160}E$, $T_{163}P$ mutant on XG-1 cells was not due to contamination by wild-type rhIL-6 because it could be inhibited by MAb CLB.IL-6/8, but not by MAb CLB.IL-6/16 (data not shown).

Figure 5:
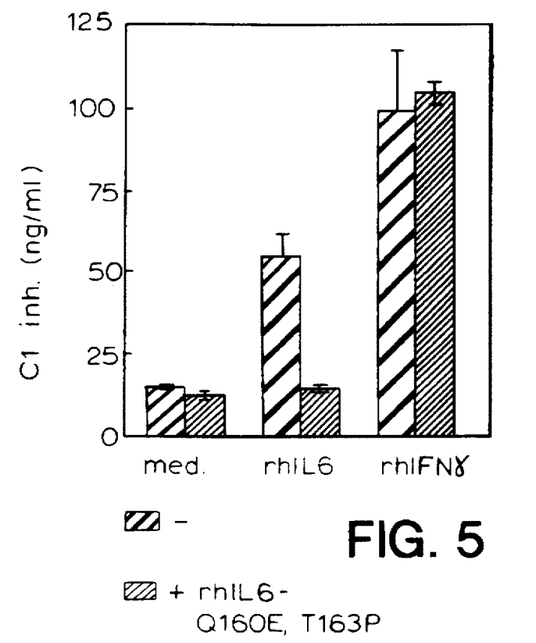
FIG. 5 shows the amount of C1 esterase inhibitor production by HepG2 cells in the presence of media, wild type IL-6 (5 ng/ml) or gamma interferon (1 ng/ml) with and without IL-6 $Q_{160}E$, $T_{163}P$.
Figure 6:
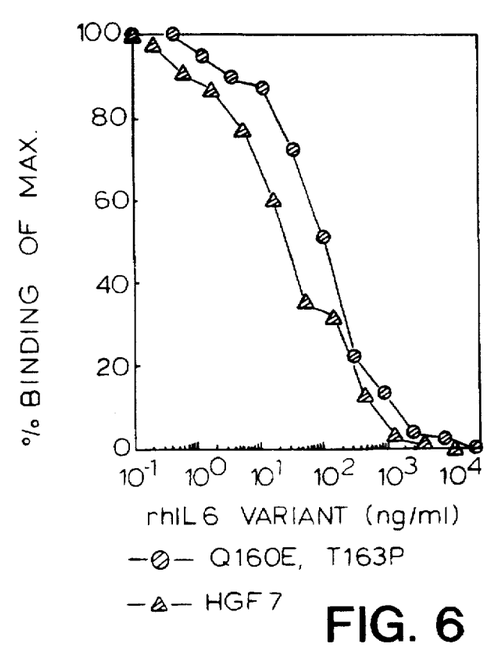
FIG. 6 compares the inhibition of IL-6 binding to IL-6 receptor-bearing cells (NIH-3T3 fibroblasts transfected with an expression vector encoding IL-6R) with rhIL-6 HGF7 and IL-6 $Q_{160}E$, $T_{163}P$.

HepG2 cells can synthesize C1 inh. in response to both IL-6 and IFN-γ via separate mechanisms (see Zuraw et al., supra). To further demonstrate the specificity of inhibition by the double-mutant, we tested whether rhIL-6 $Q_{160}E$, $T_{163}P$ could inhibit IFN-γ induced C1 inh. synthesis by the HepG2 cells. As shown in FIG. 5, the C1 esterase inhibitor synthesis induced by 5 ng/ml of rhIL-6 HGF7 was inhibited to background levels, whereas the C1 inh. synthesis induced by 1 ng/ml of IFN-γ was unimpaired.

G. IL-6R Binding of Two IL-6 Mutants

The fact that the rhIL-6 $Q_{160}E$, $T_{163}P$ could still be recognized by site I-specific MAb CLB.IL-6/8 and that it could antagonize wild-type IL-6 activity on CESS and HepG2 cells suggested that the 80 kDa binding site was still intact. To test this hypothesis binding of this variant to NIH-3T3 fibroblasts translated with an expression vector encoding the 80 kDa IL-6 receptor (see Rose-John et al., *J. Biol. Chem.* (1991) 266:3841) was compared to that of wild-type rhIL-6 in a competitive inhibition assay. FIG. 7 shows that the double-mutant was approximately 4-fold less efficient in inhibiting binding of $^{125}$I-rhIL-6 to the cells, than rhIL-6 HGF7.

TABLE 2

Specific activities (U/µg) of purified rhIL-6 variants in IL-6 bioassays

| IL-6 Variant | B9 (× 10⁻⁵) | CESS (× 10⁻³) | HepG2 | XG-1 (× 10⁻⁴) |
|---|---|---|---|---|
| mature rhIL-6 | 11 ± 3 | 5.2 ± 0.3 | 542 ± 209 | 12 ± 0.3 |
| HGF7 | 6 ± 2 | 4.7 ± 1.2 | 666 ± 165 | 4.9 ± 2.5 |
| Thr₁₆₃Pro | 2.1 ± 0.3 | 0.003 ± 0.003 | 11 ± 10 | 0.024 ± 0.0175 |
| Gln₁₆₀Glu, Thr₁₆₃Pro | 0.9 ± 0.4 | <0.001 | <0.1 | 0.004 ± 0.002 |

F. IL-6 receptor antagonistic Activity of Two IL-6 Mutants

Figure 3A:
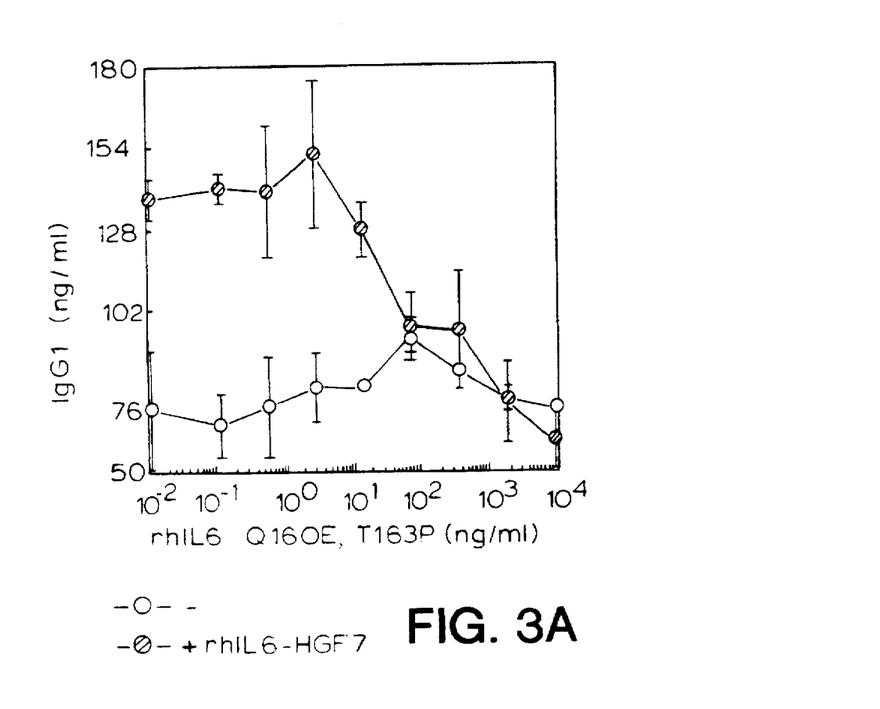
Figure 3B:
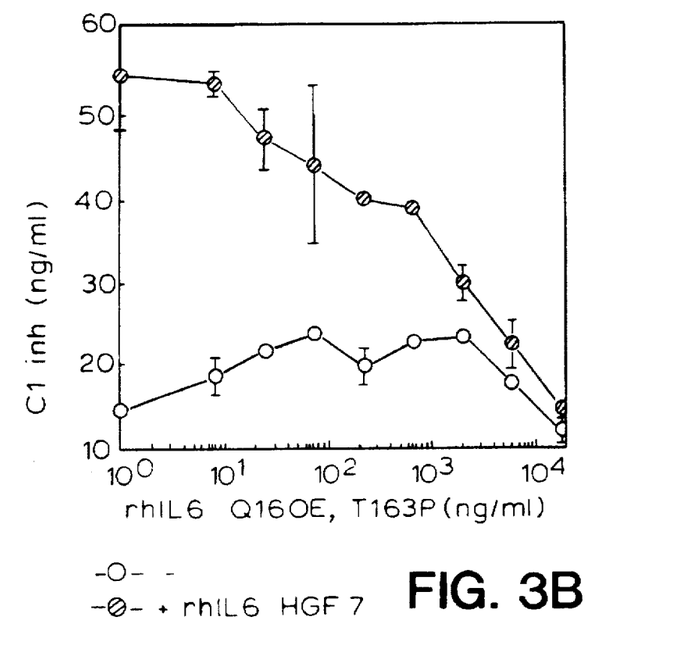
Figure 4:
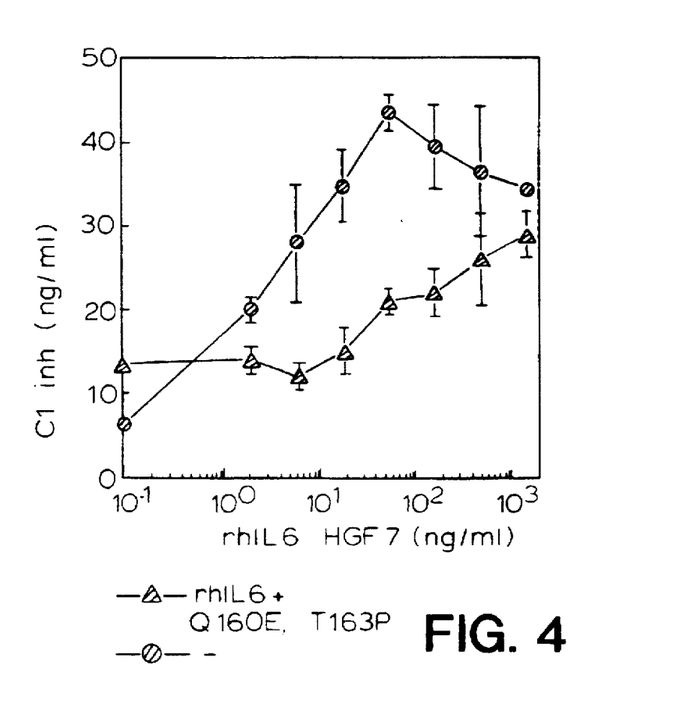
FIG. 4 shows the amount of C1 esterase inhibitor production by HepG2 cells in the presence of wild type IL-6 with and without IL-6 $Q_{160}E$, $T_{163}P$.

We tested these mutants for ability to antagonize the activity of wild-type rhIL-6 HGF7 on the cell lines. In FIG. 3a and b is shown that rhIL-6 $Q_{160}E$, $T_{163}P$ completely inhibited the wild-type IL-6 activity on CESS and HepG2 cells. In these experiments, 50% inhibition of IL-6 activity in CESS and HepG2 assays was observed with approximately 50 ng/ml and 1 µg/ml of rhIL-6 $Q_{160}E$, $T_{163}P$, respectively, corresponding to 20 and 200-fold the concentration of rhIL-6 HGF7 used to stimulate the cells. 100% inhibition was observed when the double-mutant was used in respectively 1,000 and 3,600-fold excess over wild-type. No inhibitory effects were observed on XG-1 cells. Of rhIL-6 $T_{163}P$ no antagonistic activity could be detected (data not shown). FIG. 4 shows that the inhibitory effect of rhIL-6 $Q_{160}E$, $T_{163}P$ on IL-6 activity in the HepG2 assay could be reversed by high concentrations of rhIL-6 HGF7, suggesting competitive inhibition of IL-6 receptor binding by rhIL-6 $Q_{160}E$, $T_{163}P$. A similar result was found with CESS cells (data not shown).

We claim:

1. A method of treating an IL-6 related disease comprising the step of administering to a mammal in need thereof an interleukin-6 (IL-6) receptor antagonist comprising a mutated IL-6 polypeptide comprising amino acids 30 through 185 of mature IL-6 protein, characterized by having mutations in the region corresponding to amino acid positions 154 through 163 of mature IL-6 protein, said mutations providing decreased IL-6 signal transduction activity relative to IL-6 receptor-binding activity.

2. The method of claim 1 wherein the IL-6 receptor antagonist administered is characterized by having up to three mutations in the region corresponding to amino acid positions 154 through 163 of mature IL-6 protein.

3. The method of claim 1 wherein the IL-6 receptor antagonist administered is characterized by a substitution wherein the amino acid at the position corresponding to amino acid position 163 of mature IL-6 protein is proline.

4. The method of claim 1 wherein the IL-6 receptor antagonist administered is characterized by a substitution wherein the amino acid at the position corresponding to amino acid position 160 of mature IL-6 protein is glutamic acid.

5. The method of claim 1 wherein the IL-6 receptor antagonist administered is characterized by substitutions wherein the amino acid at the position corresponding to amino acid position 163 of mature IL-6 protein is proline and the amino acid at the position corresponding to amino acid position 160 of mature IL-6 protein is glutamic acid.

6. The method of claim 1 wherein the IL-6 related disease is sepsis.

7. The method of claim 1 wherein the IL-6 related disease is multiple myeloma.

8. A method of treating an IL-6 related disease comprising the step of administering to a mammal in need thereof an interleukin-6 (IL-6) receptor antagonist comprising a mutated IL-6 polypeptide comprising amino acids 30 through 185 of mature IL-6 protein, characterized by having mutations in the region corresponding to amino acid positions 154 through 163 of mature IL-6 protein, having about the same or greater receptor-binding activity relative to mature IL-6 protein, and having about 50% or less signal transduction activity relative to mature IL-6 protein.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

GAATCTAGAT GCAATAACCA CC        22

( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

TGTCATGTCC TGCAGCCACT GGTTCTGTGC CTGC        34

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

CAGGCACAGA ACCAGTGGCT GCAGGACATG ACAA        34

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

CGAAGAGCCC TCAGGCTGGA C        21